US011439717B1

(12) United States Patent
Eggleston

(10) Patent No.: US 11,439,717 B1
(45) Date of Patent: Sep. 13, 2022

(54) UV SANITIZING DEVICE

(71) Applicant: EEH Enterprises, LLC, Bloomington, IN (US)

(72) Inventor: Richard R. Eggleston, Greenwood, IN (US)

(73) Assignee: EEH Enterprises, LLC, Bloomington, IN (US)

( * ) Notice: Subject to any disclaimer, the term of this patent is extended or adjusted under 35 U.S.C. 154(b) by 122 days.

(21) Appl. No.: 16/507,267

(22) Filed: Jul. 10, 2019

Related U.S. Application Data

(60) Provisional application No. 62/696,639, filed on Jul. 11, 2018.

(51) Int. Cl.
*A61L 2/10* (2006.01)

(52) U.S. Cl.
CPC .............. *A61L 2/10* (2013.01); *A61L 2202/11* (2013.01); *A61L 2202/16* (2013.01); *A61L 2202/25* (2013.01)

(58) Field of Classification Search
CPC ..... A61L 2/10; A61L 2202/11; A61L 2202/16
See application file for complete search history.

(56) References Cited

U.S. PATENT DOCUMENTS 6,656,424 B1 * 12/2003 Deal .................. A61L 2/10
250/455.11

OTHER PUBLICATIONS

Steris; What You Can't See Can Hurt You . . . Pathogen UV Disinfection System; Feb. 2012.
NS Medical Devices; Clorox Healthcare introduces new Optimum-UV Enlight System; Sep. 22, 2015.
The Clorox Compnay; Clorox Healthcare Announces New Optimum-UV Enlight System with Advanced Reporting Features and Powerful Performance Against Infections; Sep. 21, 2015.
SMARTUVC; Why Tru-D; from https://web.archive.org/web/20170206082623/http://tru-d.com/why-tru-d/; 2017.
SMARTUVC; Tru-D; from https://web.archive.org/web/20170203011625/http://tru-d.com/; 2017.
Canadian Healthcare Technology; Xenex given award forgerm-zapping robot; from https://www.canhealth.com; Jun. 17, 2017.
Meet Lightstrike—the robot making hospitals safer by zapping germs with UV rays; from https://www.bomtoengineer.com; Aug. 2017.
Vyas, Ami; "Germ-Zapping" Robot Aims to Make Hospitals Cleaner and Safer; from https://www.allaboutcircuits.com; Dec. 23, 2016.
Predicate Devices; Jun. 13, 2018.

* cited by examiner

*Primary Examiner* — Kevin Joyner
(74) *Attorney, Agent, or Firm* — Faegre Drinker Biddle & Reath LLP

(57) ABSTRACT

A UV sanitizing device is provided having a plurality of UV lamps. The UV sanitizing device including a timer which controls a duration of time that power is provided from the power source to the plurality of UV lamps.

4 Claims, 10 Drawing Sheets

US 11,439,717 B1

UV SANITIZING DEVICE

RELATED APPLICATION

This application claims the benefit of U.S. Provisional Application No. 62/696,639, filed Jul. 11, 2019, titled UV SANITIZING DEVICE, the entire disclosure of which is expressly incorporated by reference herein.

FIELD OF THE DISCLOSURE

The field relates to sanitizing devices, and more particularly to sanitizing devices utilizing UV light for sterilizing facilities such as hospital rooms, doctor's offices, and nursing homes.

BRIEF DESCRIPTION OF THE DRAWINGS

The features and advantages of this disclosure, and the manner of attaining them, will become more apparent and will be better understood by reference to the following description of exemplary embodiments taken in conjunction with the accompanying drawings, wherein.

Corresponding reference characters indicate corresponding parts throughout the several views. The exemplification set out herein illustrates an exemplary embodiment of the invention and such exemplification is not to be construed as limiting the scope of the invention in any manner.

DETAILED DESCRIPTION OF THE DRAWINGS

Figure 1:
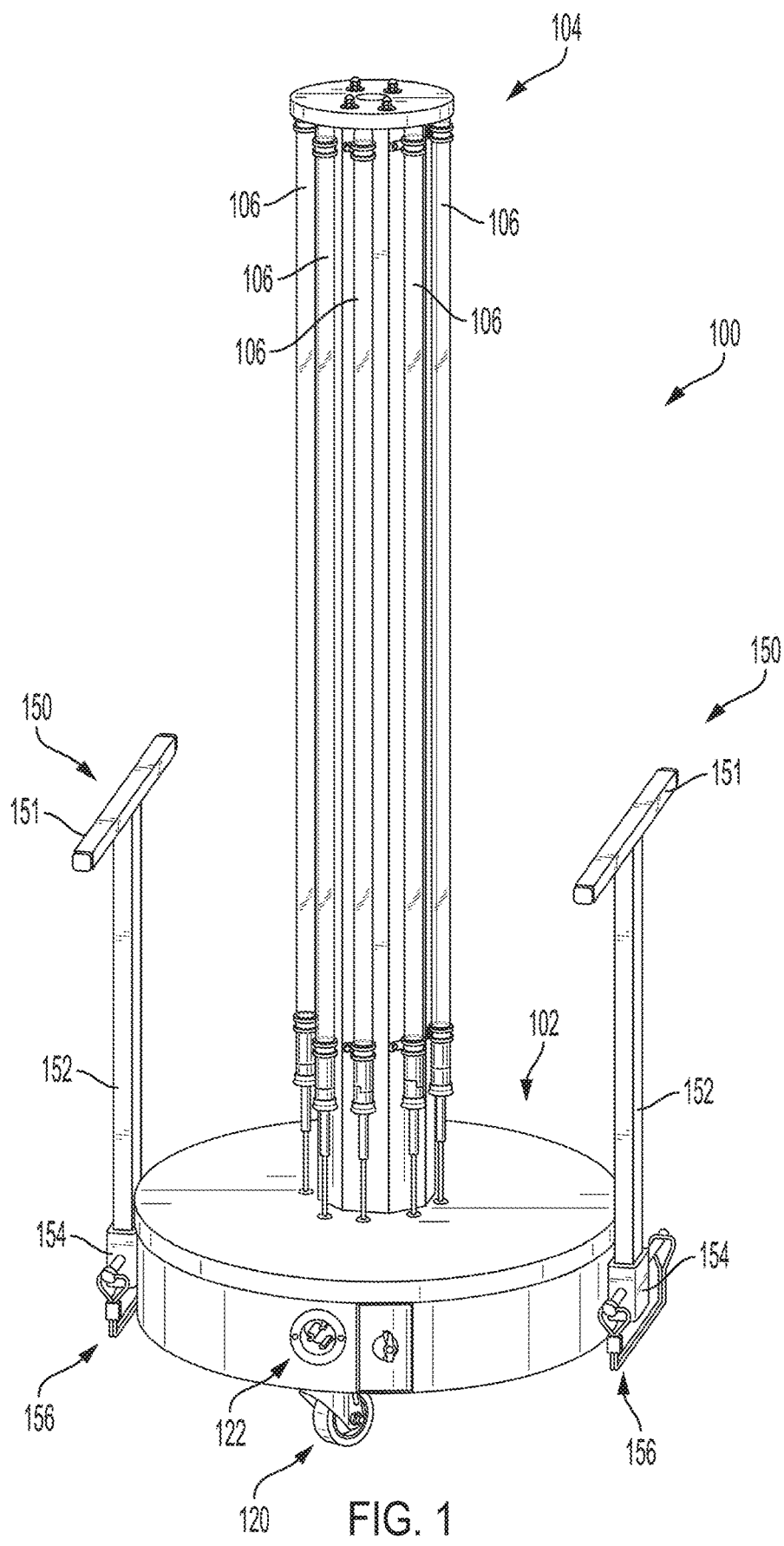
FIG. 1 illustrates a perspective view of an exemplary UV sanitizing device.
Figure 2:
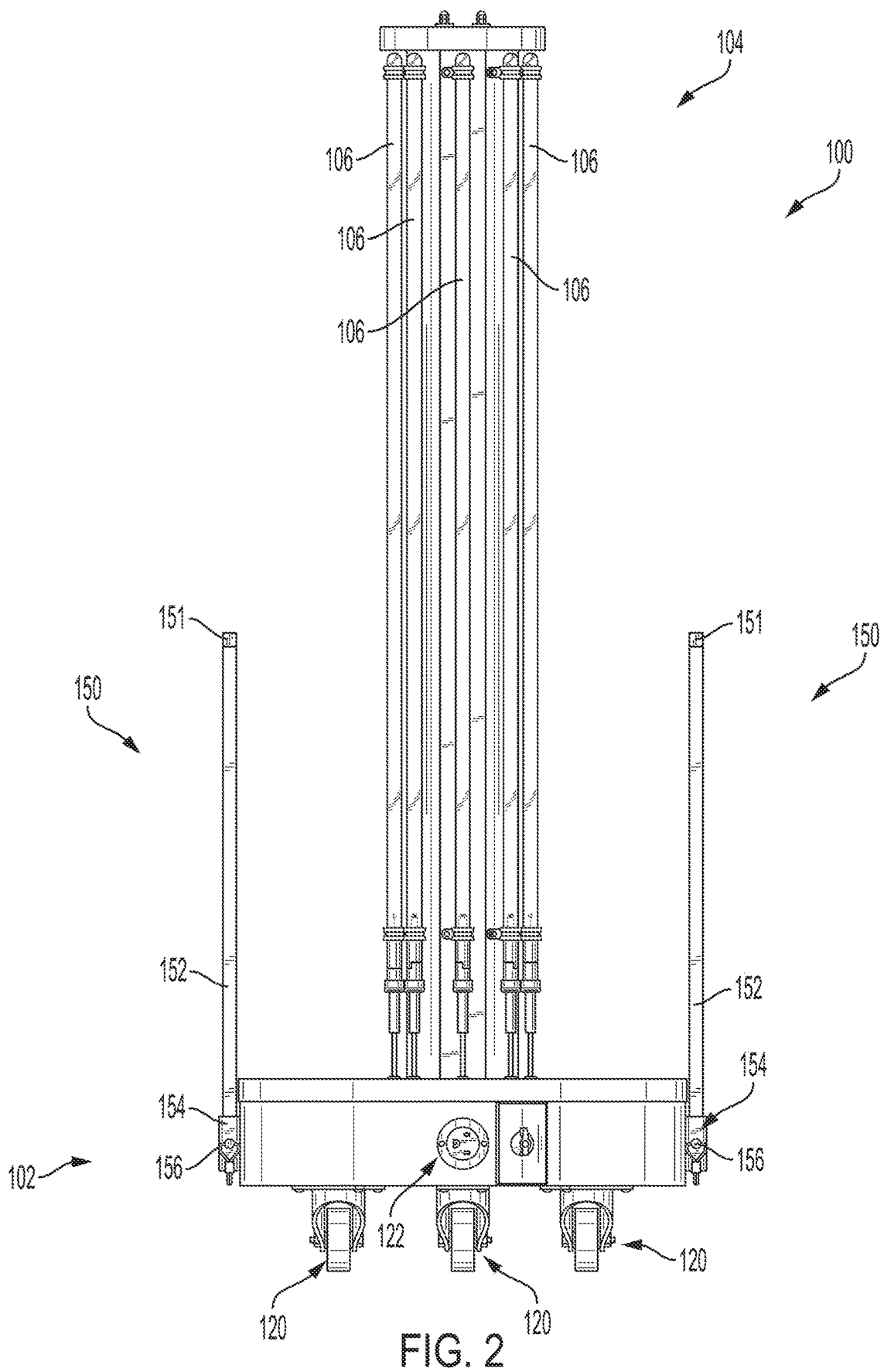
FIG. 2 illustrates a rearview of the exemplary UV sanitizing device of FIG. 1.
Figure 3:
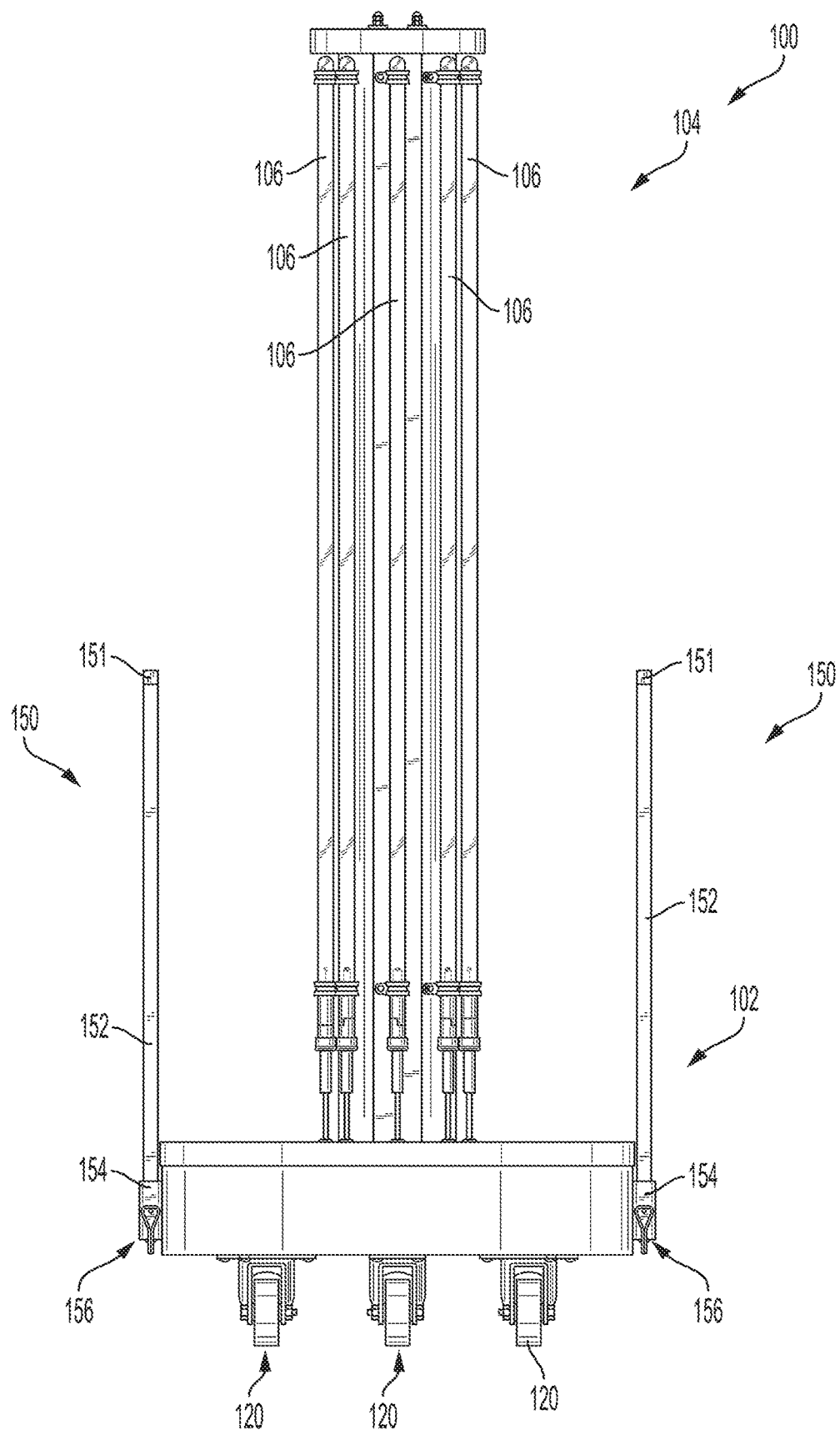
FIG. 3 illustrates a front view of the exemplary UV sanitizing device of FIG. 1.
Figure 4:
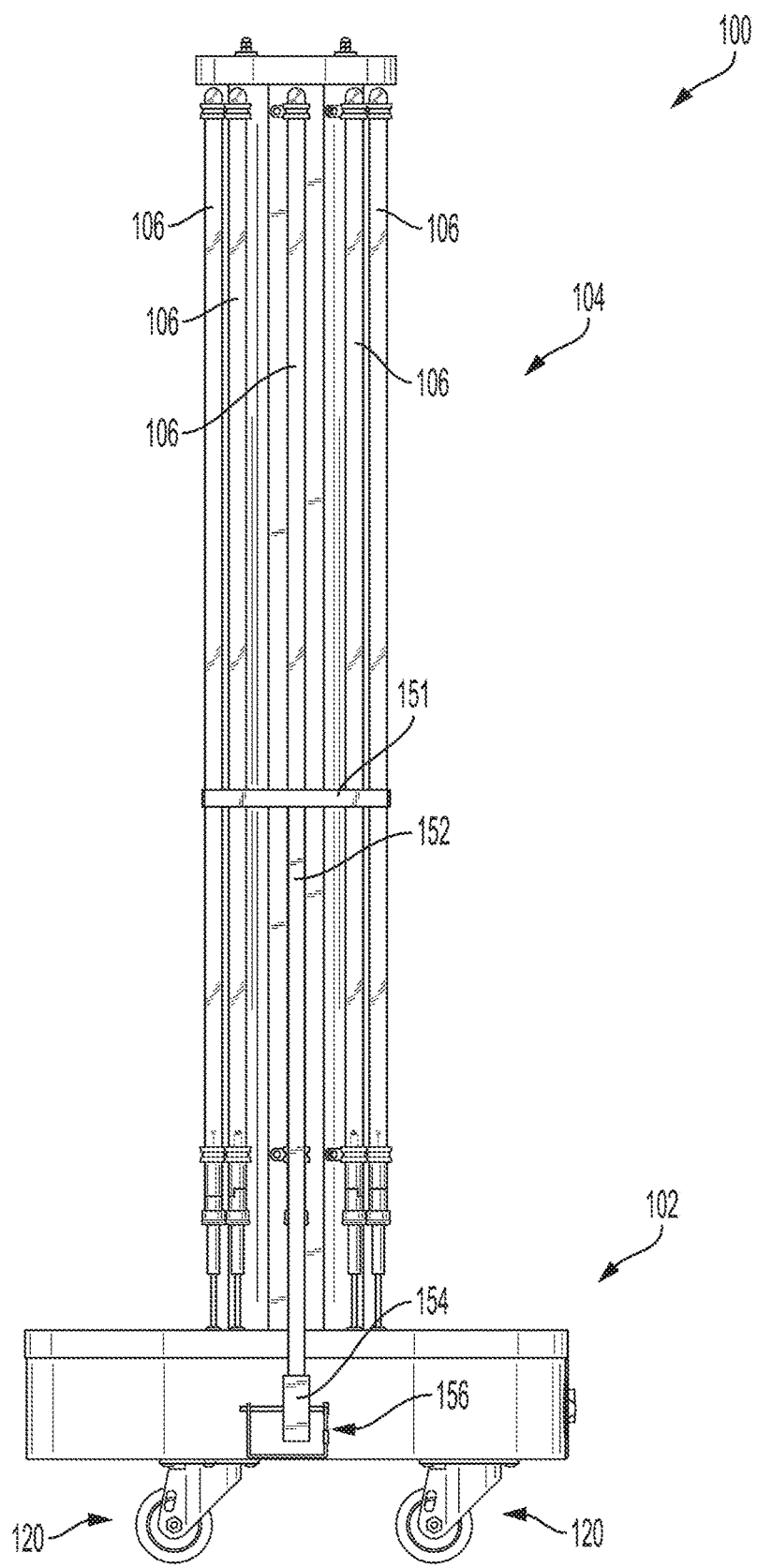
FIG. 4 illustrates a right side view of the exemplary UV sanitizing device of FIG. 1.
Figure 5:
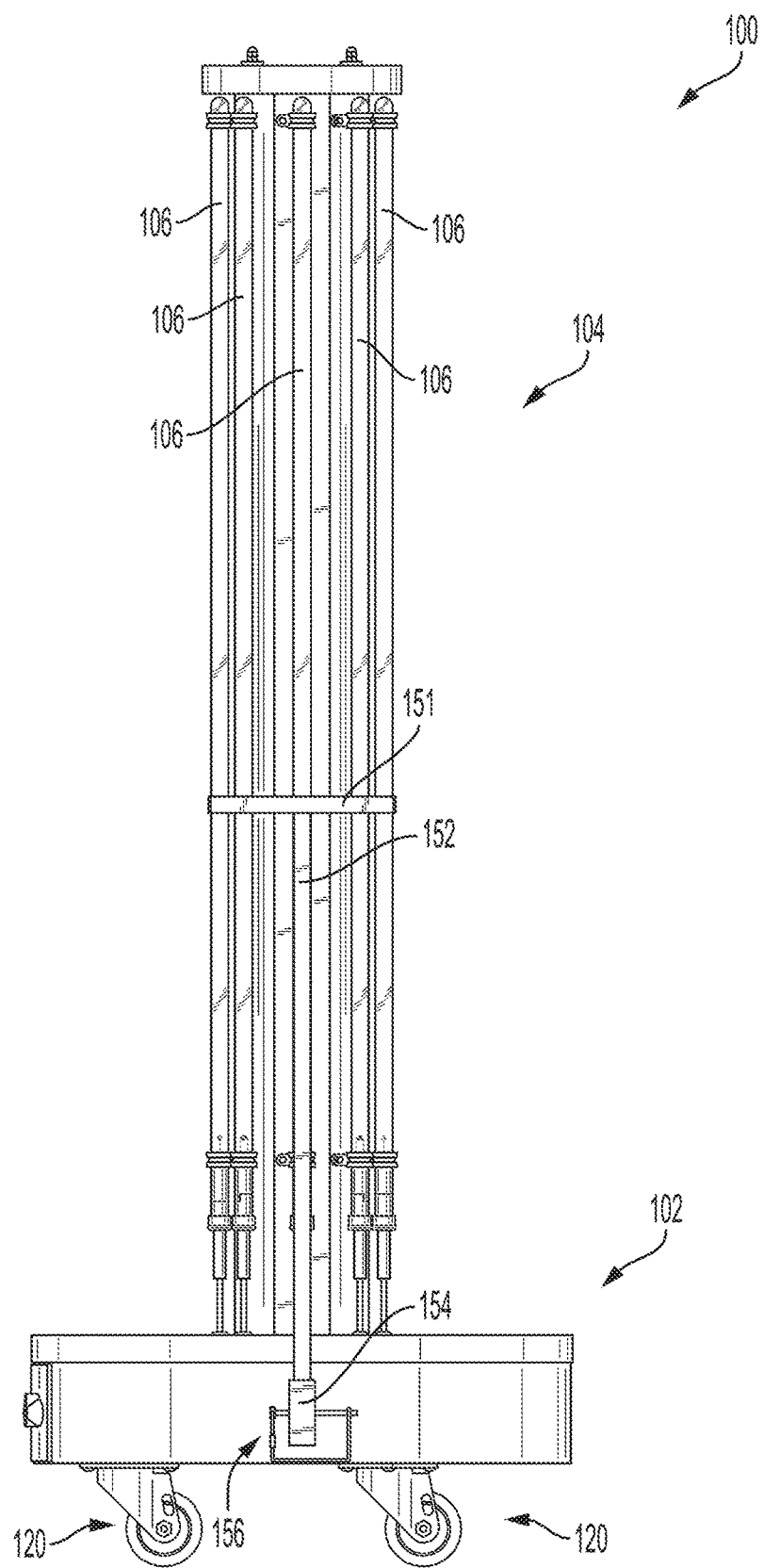
FIG. 5 illustrates a left side view of the exemplary UV sanitizing device of FIG. 1.
Figure 6:
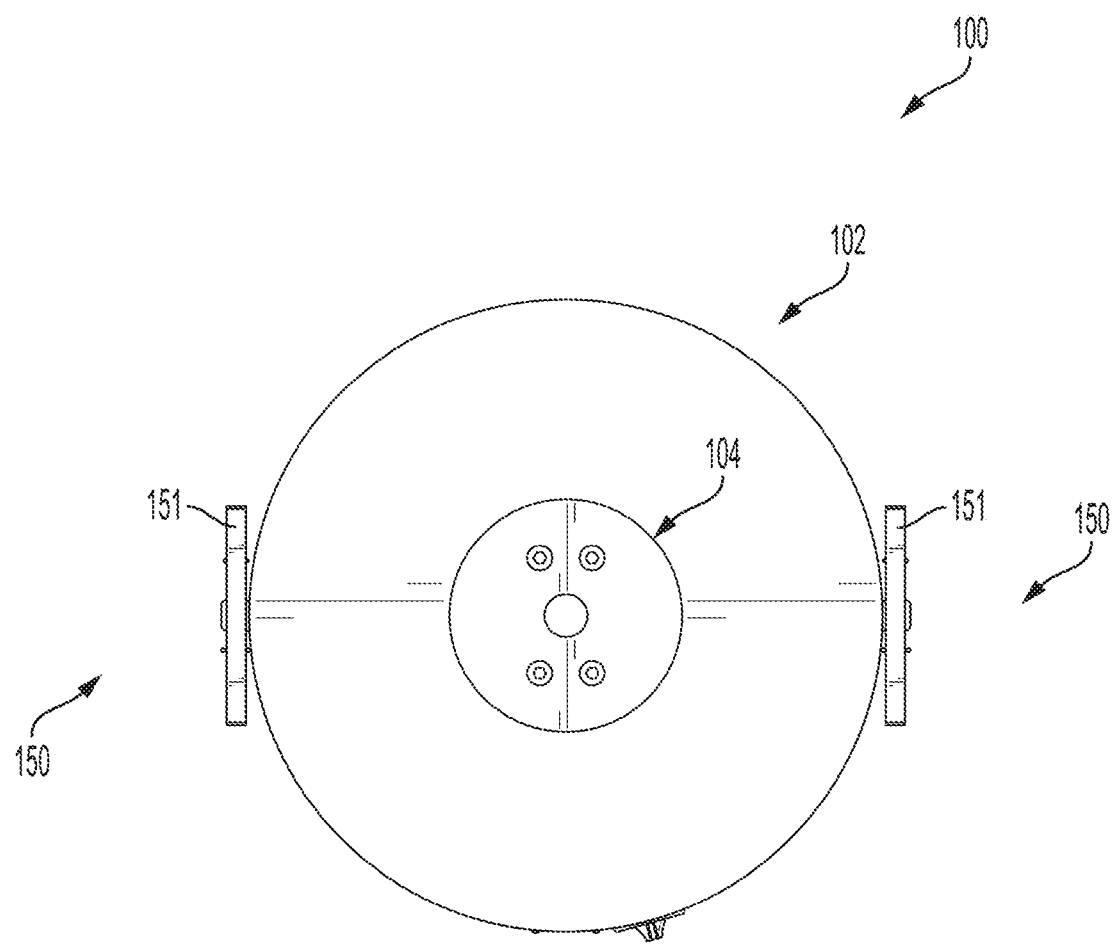
FIG. 6 illustrates a top view of the exemplary UV sanitizing device of FIG. 1.
Figure 7:
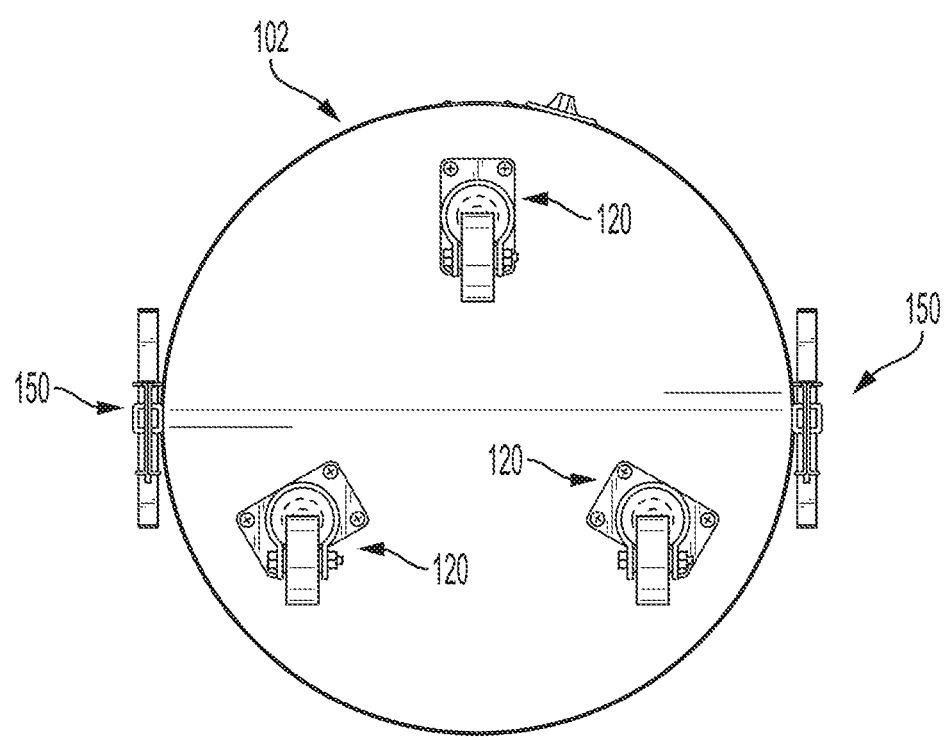
FIG. 7 illustrates a bottom view of the exemplary UV sanitizing device of FIG. 1.

For the purposes of promoting an understanding of the principles of the present disclosure, reference is now made to the embodiments illustrated in the drawings, which are described below. The embodiments disclosed herein are not intended to be exhaustive or limit the present disclosure to the precise form disclosed in the following detailed description. Rather, the embodiments are chosen and described so that others skilled in the art may utilize their teachings. Therefore, no limitation of the scope of the present disclosure is thereby intended. Corresponding reference characters indicate corresponding parts through the several views.

The terms "couples," "coupled," "coupler," and variations thereof are used to include both arrangements wherein the two or more components are in direct physical contact and arrangements wherein the two or more components are not in direct contact with each other (e.g., the components are "coupled" via at least a third component), but yet still cooperate or interact with each other.

In some instances throughout the present disclosure and in the claims, numeric terminology, such as first, second, third, and fourth, is used in reference to various components or features. Such use is not intended to denote an ordering of the components or features. Rather, numeric terminology is used to assist the reader in identifying the component or features being references and should not be narrowly interpreted as providing a specific order of components or features.

Figure 8:
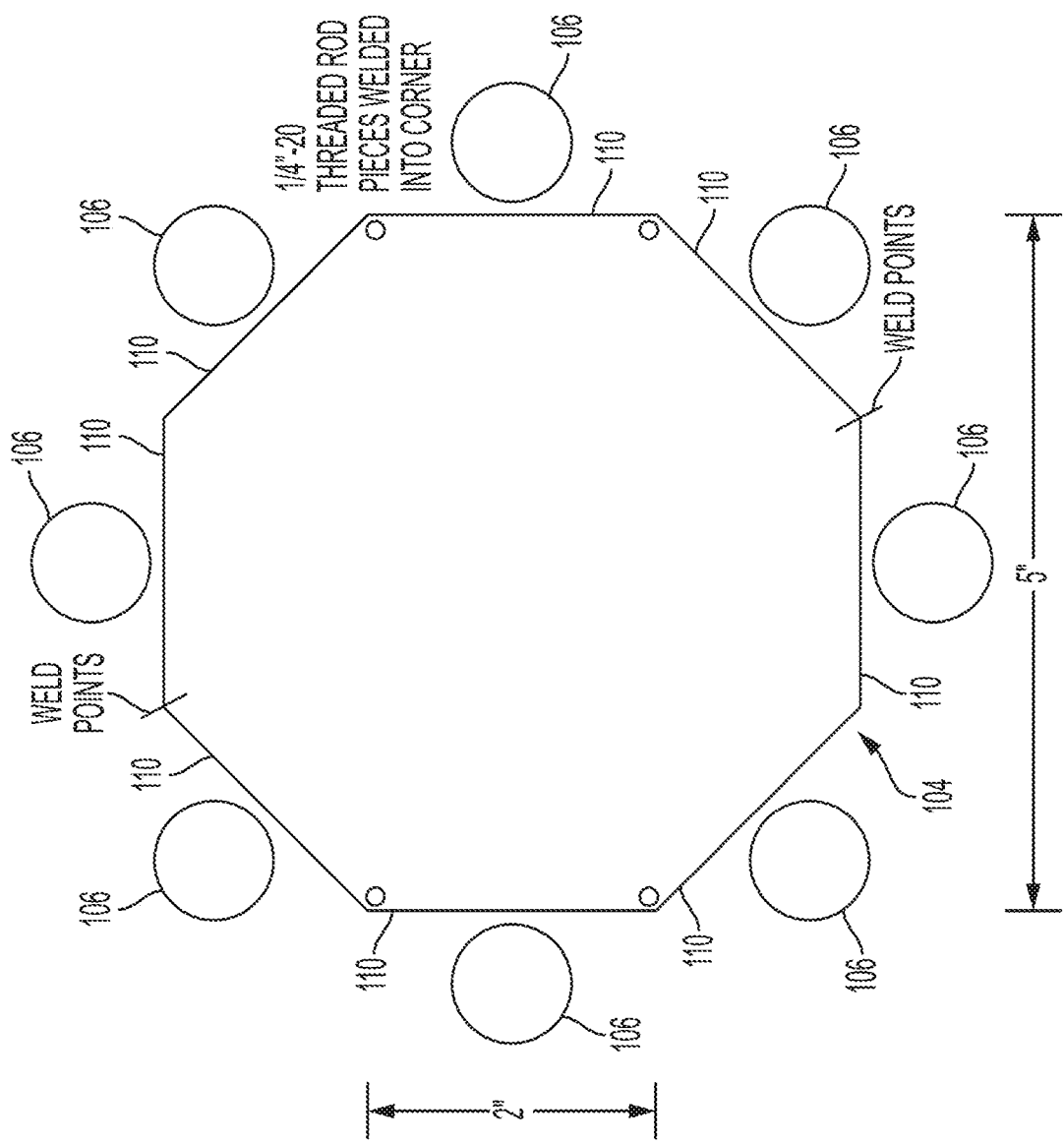
FIG. 8 illustrates a perspective view of an exemplary center column of the exemplary UV sanitizing device of FIG. 1.
Figure 9:
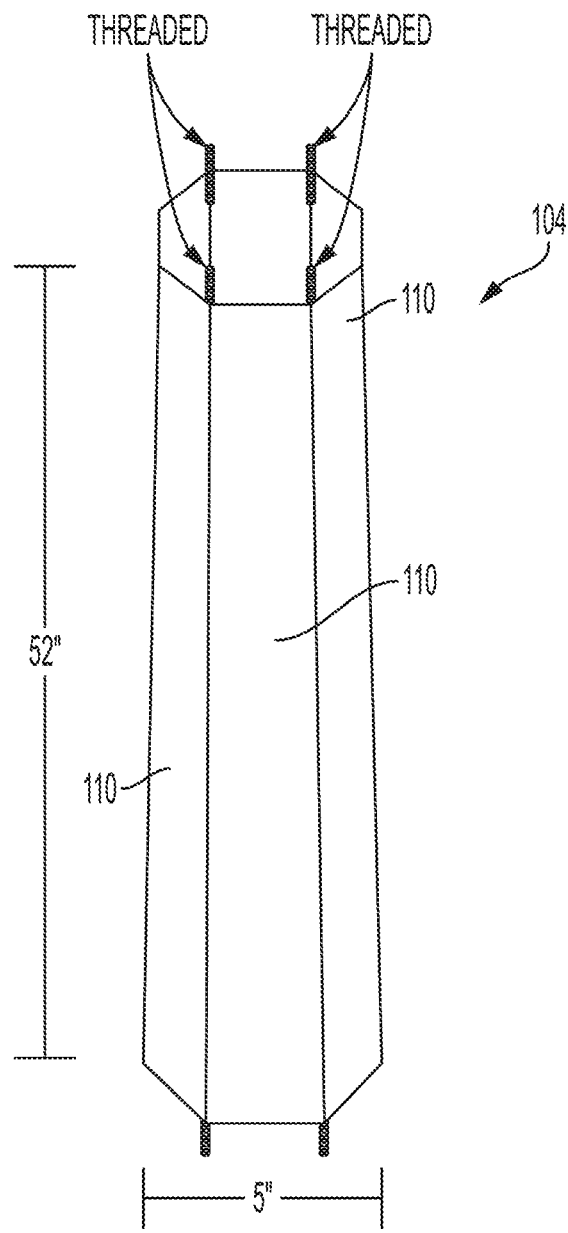
FIG. 9 illustrates a representative top view of the center column of FIG. 8.

Referring to FIGS. 1-7, an exemplary UV sanitizing device 100 is illustrated. UV sanitizing device 100 includes a base unit 102 and a tower 104 extending upward from base unit 102. Tower 104 supports a plurality of UV lamps 106. As shown in FIG. 8, tower 104 includes a plurality of faces 110 and each face 110 has associated therewith one of the plurality of UV lamps 106. FIG. 8 illustrates tower 104 having an octagonal shape. In embodiments, tower 104 may have a circular, square, triangular, or any other suitable shape. In embodiments, faces 110 of tower 104 are made of or coated or covered in an UV-reflective material.

The plurality of UV lamps 106 are positioned outboard of the faces 110 of tower 104. The plurality of UV lamps 106 are configured for a generally 360 degree delivery of UV light to the surrounding environment.

Returning to FIG. 1, base unit 102 of UV sanitizing device 100 is supported by a plurality of wheels 120. Wheels 120 aid in the movement of UV sanitizing device 100 from location to location. In the illustrated embodiment, wheels 120 are caster wheels.

Figure 10:
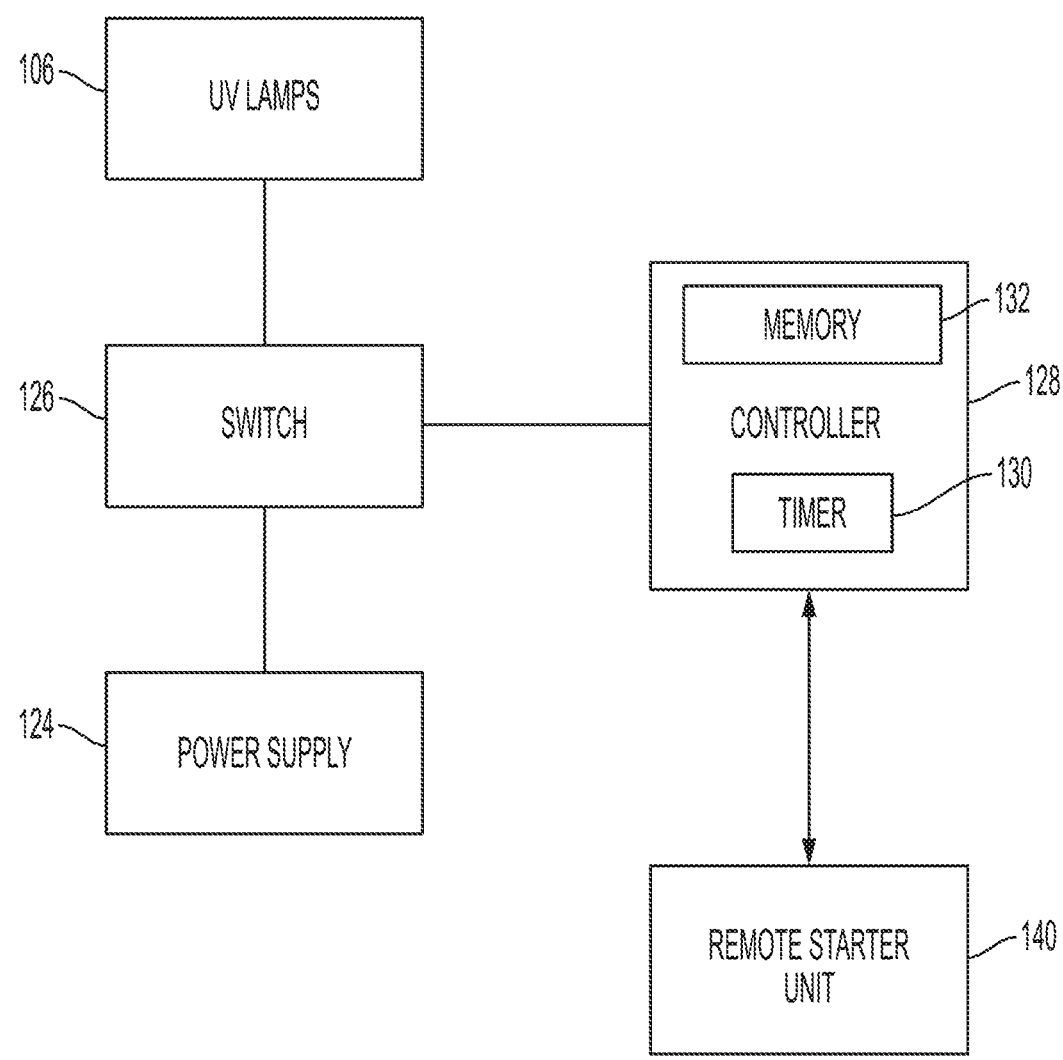
FIG. 10 illustrates a representative view of the control system and power system of the exemplary UV sanitizing device of FIG. 1.

Base unit 102 includes an electrical plug 122 to which a power supply 124 (see FIG. 10) may be connected. Referring to FIG. 10, power supply 124 provides electrical power to the plurality of UV lamps 106 through a switch 126. Switch 126 has a first state wherein electrical power is provided from power supply 124 to the plurality of UV lamps 106 at a level sufficient to power the plurality of UV lamps 106 and a second state wherein electrical power is prevented from being provided by power supply 124 to the plurality of UV lamps 106 at the level sufficient to power the plurality of UV lamps 106. In embodiments, in the second state of switch 126 no power is provided to the plurality of UV lamps 106 from the power supply 124.

In embodiments, the state of switch 126 is controlled by a controller 128. In embodiments, controller 128 is microprocessor-based and includes a non-transitory computer readable medium 132 which includes processing instructions stored therein that are executable by the microprocessor of controller 128 to control operation of switch 126 and UV sanitizing device 100. A non-transitory computer-readable medium, or memory, may include random access memory (RAM), read-only memory (ROM), erasable programmable read-only memory (e.g., EPROM, EEPROM, or Flash memory), or any other tangible medium capable of storing information.

Controller 128 may include a timer 130. In embodiments, timer 130 sets a duration of time that controller 128 places switch 126 in the first state. Timer 130 may be implemented as software and/or firmware executing on one or more programmable processors, application-specific integrated circuits, field-programmable gate arrays, digital signal processors, hardwired logic, or combinations thereof. Therefore, in accordance with the embodiments, timer 130 may be implemented in any appropriate fashion and would remain in accordance with the embodiments herein disclosed. This disclosure contemplates other embodiments in which controller 128 is not microprocessor-based, but rather is configured to control operation of switch 126 and/or UV sanitizing device 100 based on one or more sets of hardwired instructions and/or software instructions stored in a memory unit. Further, controller 128 may be contained within a single device or be a plurality of devices networked together to provide the functionality described herein.

In embodiments, controller 128 communicates with a remote starter unit 140 which provides a control signal to place switch 126 in the first state and/or to set a duration of timer 130. Remote starter unit 140 may include a plurality of user input devices to receive various user commands, such as turn on UV sanitizing device 100 and/or set a duration for operation of UV sanitizing device 100. Exemplary input devices include buttons, levers, switches, a touch display, sliders, dials, and other suitable input devices. In embodiments, remote starter unit 140 communicates with controller 128 over a wireless connection. Exemplary wireless connections include a radio frequency (RF) communication connection or an infrared (IR) communication connection.

Returning to FIG. 1, UV sanitizing device 100 further includes a pair of removable handles 150. Each removable handle includes a support portion 152 and a handle portion 151. Support portion 152 is received in an opening of a receiver 154 supported by base unit 102. Each of support portion 152 and receiver 154 include an aperture for receiving a pin of a coupler 156 which secures handle 150 to base unit 102. As illustratively shown, handle portion 151 is located at a height overlapping at least one of the plurality of UV lamps 106.

In embodiments, removable handles 150 are T-shaped. However, the removable handles may be of any other shape suitable for a handle. In embodiments, the removable handles 150 may be in a fixed position when coupled to base unit 102. In embodiments, removable handles 150 may be coupled to base unit 102 via joints that permit swiveling of removable handles 150 relative to base unit 102.

UV sanitizing device 100 is designed to kill or reduce the population of certain fungi, viruses, or bacteria and is intended to be used as a supplement (not as a replacement) to routine manual environmental cleaning and disinfection protocols, for hard non-porous environmental surfaces.

In embodiments, UV sanitizing device 100 produces UV type C optical radiation (centered around 254 nm) from UV lamps 106. In embodiments, UV sanitizing device 100 is activated by remote control to a receiving unit on a power cord. In embodiments, UV sanitizing device 100 includes a manual timer which automatically shuts off power to UV lamps 106 of UV sanitizing device 100 after a predetermined period of time. UV sanitizing device 100 is utilized to disinfect environmental surfaces by killing bacteria present on the environmental surfaces. Bacterial killing is achieved by direct exposure or reflected exposure to the UV radiation produced by UV lamps 106 of UV sanitizing device 100.

In an exemplary processing sequence of operation of UV sanitizing device 100, a qualified professional hangs the warning signage outside of the environmental area to be sanitized, such as a room. The qualified professional, using handles 150, moves UV sanitizing device 100 into a desired location of the area to be sanitized, then removes handles 150 to increase sanitizing capacity. The qualified professional sets timer 130 to a recommended exposure time based on the square footage of room to be sanitized. The qualified professional connects a remote plug into electrical plug 122 on base unit 102 of UV sanitizing device 100 and then connects the remote plug into a wall outlet. The qualified professional vacates the room to be sanitized, shuts the door to the room, and uses remote starter unit 140 to start the operation of UV sanitizing device 100. When timer 130 reaches the desired duration, the UV emission of UV lamps 106 of UV sanitizing device 100 is stopped.

In an exemplary embodiment of the present disclosure, a UV sanitizing device is provided. The UV sanitizing device comprises a plurality of wheels; a base unit supported by the plurality of wheels; a central tower extending upward from the base unit, the central tower having a faceted exterior; a plurality of UV lamps supported by the base unit, wherein each facet of the faceted exterior of the central tower is overlapped by at least one respective UV lamp of the plurality of UV lamps; at least one removable handle coupled to the base unit, the at least one removable handle extending upward from the base unit to a height overlapping at least one of the plurality of UV lamps; and a controller operatively coupled to the plurality of UV lamps to control power provided to the plurality of UV lamps, the controller including a timer which limits power provided to the plurality of UV lamps to a first time period.

In another exemplary embodiment of the present disclosure, a method for sanitizing a room is provided. The method comprising the steps of positioning a wheeled UV sanitizing device in a room by rolling the wheeled UV sanitizing device into the room, the wheeled UV sanitizing device including a plurality of UV lamps; connecting the wheeled UV sanitizing device to a power source; setting a timer supported by the wheeled UV sanitizing device, the timer controlling a duration of time that power is provided from the power source to the plurality of UV lamps; starting a provision of power from the power source to the plurality of UV lamps from a location outside of the room; and ending the provision of power from the power source to the plurality of UV lamps based on the expiration of the duration of time of the timer.

The attached Appendix discloses many additional aspects of embodiments of UV sanitizing device 100 and the contents thereof form part of this disclosure. An advantage, among others, of UV sanitizing device 100 is the use of a timer.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. A UV sanitizing device, comprising:
   a plurality of wheels;
   a base unit supported by the plurality of wheels;
   a central tower extending upward from the base unit, the central tower having a faceted exterior;
   a plurality of UV lamps supported by the base unit, wherein each facet of the faceted exterior of the central tower is overlapped by at least one respective UV lamp of the plurality of UV lamps;
   at least one removable handle coupled to the base unit, the at least one removable handle extending upward from the base unit to a height overlapping at least one of the plurality of UV lamps;

a controller operatively coupled to the plurality of UV lamps to control power provided to the plurality of UV lamps; and a remote starter in wireless communication with the controller, the remote starter being configured to receive a duration command via an input device operated by a user;

wherein the controller is configured to receive the duration command over a wireless connection with the remote starter and respond by setting a timer which limits power provided to the plurality of UV lamps to a first period of time indicated by the duration command.

2. The UV sanitizing device of claim 1, wherein the duration command is based on a square footage of a room to be sanitized.

3. A method for sanitizing a room, comprising the steps of:

positioning a wheeled UV sanitizing device in a room by rolling the wheeled UV sanitizing device into the room, the wheeled UV sanitizing device including a plurality of UV lamps;

connecting the wheeled UV sanitizing device to a power source;

inputting a duration command via an input device of a remote starter configured to wirelessly communicate with the wheeled UV sanitizing device;

receiving the duration command at the wheeled UV sanitizing device over a wireless connection;

responding to receipt of the duration command at the wheeled UV sanitizing device by setting a timer supported by the wheeled UV sanitizing device, the timer controlling a duration of time that power is provided from the power source to the plurality of UV lamps;

starting a provision of power from the power source to the plurality of UV lamps from a location outside of the room; and ending the provision of power from the power source to the plurality of UV lamps based on the expiration of the duration of time of the timer.

4. The method of claim 3, wherein the duration command is based on a square footage of the room to be sanitized.

\* \* \* \* \*